US00RE39915E

(19) United States
(12) Reissued Patent
Rittersdorf et al.

(10) Patent Number: US RE39,915 E
(45) Date of Reissued Patent: Nov. 6, 2007

(54) METHOD FOR THE DETERMINATION OF HDL CHOLESTEROL BY MEANS OF A RAPID DIAGNOSTIC AGENT WITH AN INTEGRATED FRACTIONATING STEP

(75) Inventors: Walter Rittersdorf, Mannheim (DE); Ulfert Deneke, Rimbach (DE); Gerhard Hiller, Mannheim (DE); Hartmut Merdes, Heidelberg (DE); Klaus Buecker, Viernheim (DE); Uwe Goebbert, Mannheim (DE)

(73) Assignee: Roche Diagnostics GmbH, Mannheim (DE)

(21) Appl. No.: 10/644,617

(22) Filed: Aug. 20, 2003

Related U.S. Patent Documents

Reissue of:
(64) Patent No.: 6,171,849
Issued: Jan. 9, 2001
Appl. No.: 09/481,664
Filed: Jan. 12, 2000

U.S. Applications:
(

(62) Division of application No. 09/114,361, filed on Jul. 14, 1998, now Pat. No. 6,214,570, which is a continuation of application No. 08/661,833, filed on Jun. 11, 1996, now Pat. No. 5,786,164, which is a division of application No. 08/384,046, filed on Feb. 6, 1995, now Pat. No. 5,580,743, which is a division of application No. 07/572,875, filed on Aug. 24, 1990, now Pat. No. 5,426,030.

(30) Foreign Application Priority Data

Sep. 1, 1989 (DE) ..... 39 29 032

(51) Int. Cl.
*C12M 1/00* (2006.01)
*C12M 1/36* (2006.01)
*C12M 1/34* (2006.01)

(52) U.S. Cl. ..... 435/283.1; 435/286.5; 435/286.1; 435/287.1

(58) Field of Classification Search ..... 435/283.1, 435/286.5, 286.1, 287.1
See application file for complete search history.

(56) References Cited

U.S. PATENT DOCUMENTS

| | | | |
|---|---|---|---|
| 4,414,326 | A | 11/1983 | Goldberg |
| 4,477,575 | A | 10/1984 | Vogel et al. |
| 4,604,264 | A | 8/1986 | Rothe et al. |
| 4,746,605 | A | 5/1988 | Kerscher et al. |
| 4,870,005 | A | 9/1989 | Akiyoshi et al. |
| 4,876,067 | A | 10/1989 | Deneke et al. |
| 5,135,716 | A | 8/1992 | Thakore |
| 5,213,964 | A | 5/1993 | Jones |
| 5,213,965 | A | 5/1993 | Jones |
| 5,286,626 | A | 2/1994 | Law et al. |
| 5,316,916 | A | 5/1994 | Jones |
| 5,401,466 | A | 3/1995 | Foltz et al. |
| 5,407,836 | A | 4/1995 | Ziegenhorn et al. |
| 5,411,870 | A | 5/1995 | Law et al. |
| 5,426,030 | A | 6/1995 | Rittersdorf et al. |
| 5,460,974 | A | 10/1995 | Kozak et al. |
| 5,532,172 | A | 7/1996 | Ziegenhorn et al. |
| 5,580,743 | A | 12/1996 | Rittersdorf et al. |
| 5,786,164 | A | 7/1998 | Rittersdorf et al. |

FOREIGN PATENT DOCUMENTS

| | | |
|---|---|---|
| DE | 3 029 579 A1 | 2/1982 |
| DE | 31 30 749 A1 | 2/1983 |
| DE | 3 630 999 A1 | 3/1988 |
| EP | 0 045 476 A1 | 2/1982 |
| EP | 0 319 250 A1 | 6/1989 |
| EP | 0 408 223 A1 | 1/1991 |

OTHER PUBLICATIONS

G. Russell Warnick, "Measurement of Cholesterol, Trigiycerides, and HDL Using Compact Analysis Systems," *Clinics in Laboratory Medicine*, vol. 9: No. 1, (Mar. 1989).
Paul S. Bachorik et al., "Precipitation Methods for Quantification of Lipoproteins," *Methods in Enzymology*, vol. 129:78–100 (1986).
Gerhard Hiller et al., "HDL Cholesterol on the Reflotron® System," *Clin. Chem.*, 33(6):895–896 (1987).
Derwent Abstract 88–061491, 1988.
Derwent Abstract 90–295783, 1990.
Walter J. Weber, Jr., "Physicochemical Process," Willey–Interscience, NY 1972, p. 131.

*Primary Examiner*—Ralph Gitomer
(74) *Attorney, Agent, or Firm*—Fulbright & Jaworski LLP

(57) ABSTRACT

An apparatus comprising a first porous carrier and a second porous carrier for evaluating biological fluid samples is disclosed. The apparatus is used for separating non high density lipoprotein (non-HDL) from a lipoprotein in a body sample and for determining high density lipoprotein (HDL) cholesterol in a HDL and non high density lipoprotein (non-HDL) in a body sample.

6 Claims, 1 Drawing Sheet

Figure 1:
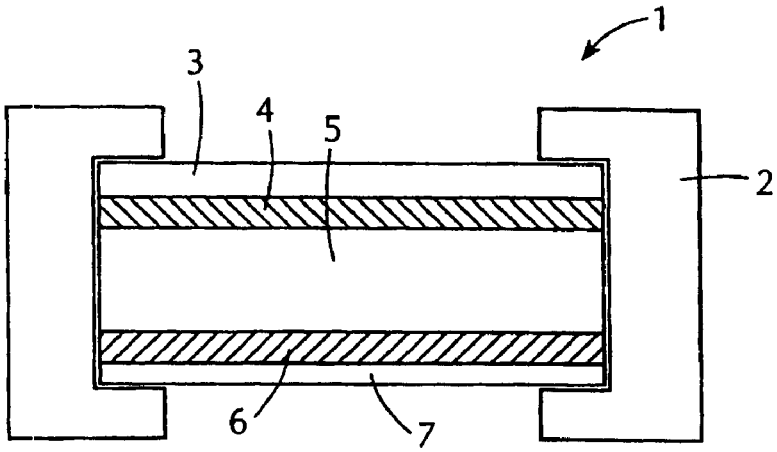

METHOD FOR THE DETERMINATION OF HDL CHOLESTEROL BY MEANS OF A RAPID DIAGNOSTIC AGENT WITH AN INTEGRATED FRACTIONATING STEP

Matter enclosed in heavy brackets [ ] appears in the original patent but forms no part of this reissue specification; matter printed in italics indicates the additions made by reissue.

[This application is a Division of Ser. No. 09/114,361 filed Jul. 14, 1998 which is a continuation of Ser. No. 08/661,833 filed Jun. 11, 1996 now U.S. Pat. No. 5,786, 164.] *This application is a Reissue of Ser. No. 09/481,664 filed Jan. 12, 2000, now U.S. Pat. No. 6,171,849, which is a divisional of Ser. No. 09/114,361 filed Jul. 14, 1998, now U.S. Pat. No. 6,214,570, which is a continuation of Ser. No. 08/661,833 filed Jun. 11, 1996, now U.S. Pat. No. 5,786,164, which is a divisional of Ser. No. 08/384,046 filed Feb. 6, 1995, now U.S. Pat. No. 5,580,743, which is a divisional of Ser. No. 07/572,875 filed Aug. 24, 1990, now U.S. Pat. No. 5,426,030, which claims priority to German application No. 39 29 032 filed Sep. 1, 1989.*

The invention concerns a method for the quantitative determination of HDL (High Density Lipoprotein) in biological fluids and an agent suitable thereof.

Total cholesterol in blood, plasma or serum is one of the best known parameters for assessing the extend of risk of a coronary heart disease. However, the concentration of total cholesterol is only of limited value for the assessment of individual risk. The measurement of the cholesterol in the lipoprotein of low density (Low Density Lipoproteins= LDL) on the one hand and in the lipoproteins of high density (High Density Lipoproteins=HDL) on the other hand is more meaningful. Epidemiological and clinical studies have shown that there is a positive correlation between LDL cholesterol and coronary heart disease and a negative correlation between HDL cholesterol and coronary heart disease.

As a close approximation the determination of the HDL as well as the total cholesterol is sufficient for an assessment of risk. This course is preferably followed at present in diagnostic practice.

The other lipoprotein classes (LDL, VLDL, chylomicrons) which are present have to be separated in order to determine HDL cholesterol separately. The potential methods of separation are based on differences in the flotation densities (sequential flotation or equilibrium sedimentation, both in the ultracentrifuge), on different surface charges (electrophoreses on paper or agarose as carrier) or on differences in the apolipoproteins (immunochemical methods using specific antibodies). All these methods of separation are expensive, time-consuming and not established in routine laboratories. Precipitation reactions (in Monographs on Atherosclerosis, Vol. II (1982), Clackson, T. B., Kritchevsky, D., Pollak, O. J. eds: Lipoprotein Precipitation, Burstein, M., Legmann, P. and in Meth. in Enzymology, Vol. 129 (1986)) whose specificity depends on the particle dimension and the surface charge are cheap, relatively easy to handle and therefore widespread. Polymeric substances serve as precipitation reagents, and these are usually of a polyanionic nature. Polymers which are uncharged are also suitable. The polyanions usually need bivalent cations in order to develop their precipitating effect, while the uncharged polymers do not require them.

The experimental procedures and the concentrations which are used for the combined precipitation agents are designed to quantitatively precipitate all lipoproteins except HDL, to separate these precipitates from the liquid fraction of the sample in a suitable manner and subsequently to quantify the HDL in the liquid fraction of the sample by means of a cholesterol assay. For this, depending on how the test is carried out, a defined volume of precipitating agent (in suitable concentrations) is mixed intensively with a defined volume of the sample to be determined. It is the state of the art to allow a reaction time of at least 10 minutes for the precipitation and only after this time interval has elapsed to separate sedimented non-HDL lipoprotein precipitates and HDL remaining in the liquid fraction by centrifugation. The centrifugation step also needs some time.

This method is much too time-consuming for a routine test. In addition, centrifugation steps with subsequent separation of the supernatant need complicated additional equipment and a transfer step. The required pipetting procedure in which a defined amount of supernatant is taken is, in addition, a source of error which can lead to less precise measurements.

It is therefore the object of the invention to avoid the disadvantages of the state of the art and to provide a method for the separation of non-HDL lipoproteins from biological fluids which can be carried out more rapidly and without complicated additional equipment and which allows a more rapid and a simpler HDL cholesterol determination.

The object is achieved by a method for the separation of non-HDL lipoproteins from biological fluids, in which the biological fluid containing non-HDL lipoproteins is applied onto a carrier through which liquids can flow and which contains a precipitating agent for non-HDL lipoproteins. The invention also provides an agent for the separation of non-HDL lipoproteins and a rapid diagnostic agent which contains this agent.

It was found that the precipitation of the non-HDL lipoproteins proceeds particularly rapidly and specifically with conventional, well-known precipitating agents when these precipitating agents are applied in a finely dispersed form onto a carrier through which liquids can flow and the sample has to flow through this carrier. In general, the precipitation takes less than 1 min. Carriers through which liquids can flow are: papers, fabrics made of synthetic fibres such as e.g. polyester or polyamide or others, fabrics made of natural fibres such as cotton, silk or others or mixtures of these materials. In this connection, the structure of the fabrics can be monofilament or multifilament, multifilament forms being preferred.

The fibres which compose the carrier through which liquids can flow preferably have a fibre diameter from 3 to 100 μm, preferably 5 to 50 μm. The carrier has in particular a weight per unit area of 10 to 100 g/m$^2$, preferably 10 to 50 g/m$^2$ at a thickness of 0.030 to 0.150 mm, and the ability to absorb water is 25 to 100 g/m$^2$, preferably 40 to 70 g/m$^2$ at the thicknesses mentioned above.

Other suitable carriers are arrangements of glass fibres and mixtures of glass fibres with the fibres mentioned above through which liquids can flow—preferably in the form of fleece—and membranes in different forms. The membranes should have hydrophilic properties, a thickness between 20–250 μm, preferably 70–150 μm and pore sizes between 0.2–20 μm, preferably 5–15 μm.

The transport of liquid in these carriers is based on capillary forces.

The precipitating agents are preferably applied to the carrier by impregnating the carrier with a solution, emulsion or suspension of the precipitating agent and subsequent drying. In this process other useful additives such as pH buffer substances or detergents etc. can also be applied.

In this construction all chemical compounds are suitable as precipitating agents which can also be used in a "wet chemical" process for the precipitation of lipoproteins as long as they dissolve quickly enough in the sample solution. Certain polyanions in combination with bivalent cations are in particular known. Examples of these include combinations of phosphotungstic acid and magnesium chloride, of heparin and manganese (II) chloride or of dextran sulphate and magnesium chloride. It should be noted that, in principle, each polyanion can be combined with each of the three cations ($Mg^{2+}$, or $Mn^{2+}$, or $Ca^{2+}$) which results, however, in slight differences in their capacity to precipitate lipoproteins (Burstein, 1986). The concentration of the chosen cation can be adapted accordingly in order to specifically precipitate the non-HDL lipoproteins. The molecular size of the polyanion used also influences the capacity to precipitate lipoproteins and should be taken into account when choosing the concentrations. The use of dextran sulphate with a molecular weight of 500000 and 50000, for example, is known. Both are also suitable for an application on carriers through which liquids can flow. Dextran sulphate with a molecular weight of 50000 combined with $Mg^{2+}$ is, however, preferred in which case $Mg^{2+}$ is preferably used in the form of magnesium acetate. In principle, magnesium sulphate, magnesium chloride and magnesium aspartate can also be used.

The concentration of the precipitating agent can be matched exactly to the volume of the sample to be examined.

The non-HDL lipoproteins are precipitated by bringing a sample into contact with the carrier through which liquids can flow and which contains the precipitating agent. The precipitation reaction is started thereby. The time interval during which the sample is in contact with the precipitating agent on the precipitating agent carrier can be adjusted in a simple manner by varying the suction pressure by means of the interstitial volumes or the hydrophilicity of the carrier. The achieved flow rates of the sample through the carrier are very important for the test performance. The precipitate formation is completed after less than one minute, at best even after ca. 10 sec and the liquid can be removed from the carrier material. This can be effected continuously or discontinuously, for example by decanting, using gravitational force or by aspirating. The fluid is preferably drawn into a further carrier by capillary forces in which the precipitated non-HDL lipoproteins are separated. This process requires that the carriers are in contact with one another. The separation of the precipitates by other methods such as centrifugation is less preferable even though this is also possible without losing the advantage of the fast precipitation.

It was found that lipoprotein precipitates which are formed by the action of a combination of polyanions and the bivalent carbons mentioned above on biological samples can be retained in a mesh of fibres.

The arrangement of the fibres in the mesh is preferably disordered. Glass fibres, cellulose fibres, polyamide fibres and polyester fibres or mixtures thereof are preferably used as the fibres. Glass fibres and mixtures with the fibres mentioned above are particularly preferred. The fibres which make up the mesh preferably have a diameter of 0.2 to 10.0 μm, preferably a diameter of 0.5 to 5.0 μm. The mesh has a weight per unit area of 20 to 50 $g/m^2$, preferably 23 to 30 $g/m^2$ and a capacity to absorb water of 250 to 500 $g/m^2$, preferably of 32o to 42o $g/m^2$ thickness of 0.19 to 0.23 mm.

Systems containing glass fibres, their possible spatial arrangement and the dimension of the fibres are described in detail in DE 30 29 579. Furthermore, the mesh of fibres can be hardened by the addition of suitable binding agents, either of an inorganic nature (e.g. water glass) or organic nature (e.g. polymers such as polyvinyl acetate, polyacrylic acid ester or similar polymers). These additives inter alia agglutinate the fibres at those positions where they are in contact with one another and in this way they improve the mechanical stability of the fibre mesh.

The liquid fraction of the applied sample spreads unhindered through the whole mesh and it can also leave it when the geometric arrangement is approximately arranged or configured or by overcoming the internal capillary forces of the mesh. In this way the separation of precipitated non-HDL lipoproteins and non-precipitated HDL can be achieved with simple devices. Biological fluids from which the non-HDL lipoproteins can be separated according to the present invention include whole blood, serum and plasma.

The method can be particularly advantageously used in methods for the quantitative determination of HDL cholesterol on test strips. For this, the fluid from which the non-HDL lipoproteins have been separated according to the method described above, is brought into contact with reagents which are necessary and/or useful for carrying out the test reaction, for example a test reaction for cholesterol. Such reagents are known to the expert, for example from EP-B-0016387, and can be adapted to the expected cholesterol concentrations (0–100 mg/dl). They can for example, also be present in the form of a film or a coating on a porous carrier. Such embodiments of reagent forms are known to the man skilled in the art.

An embodiment of a method for the determination of HDL cholesterol which contains the preferred embodiment for separating the non-HDL lipoproteins is shown in FIG. 1. A rapid diagnostic agent (1) contains several layers of a carrier in a casing (2).

A fibre mesh (5) with a separating capacity for lipoprotein precipitates which is adjusted to the chosen sample volume is underneath a carrier through which liquids can flow and which is impregnated with a precipitating agent (4). Adjoining this is a suitable absorptive cholesterol determining test film (6) which is capable of taking up fluid free of precipitate from the fibre mesh. The test film is coated on a transparent foil (7). The determination is started by applying the sample liquid over the carrier containing the precipitating agent. The measurement signal which develops can be evaluated visually or photometrically from the foil side of the construction.

This simple design is not well-suited for the investigation of whole blood. If whole blood is to be used, then the cellular blood components are preferably separated in a layer (3) in front of the carrier for the precipitating agent e.g. by agents which are described in detail in DE-A-30 29 579.

Figure 2:
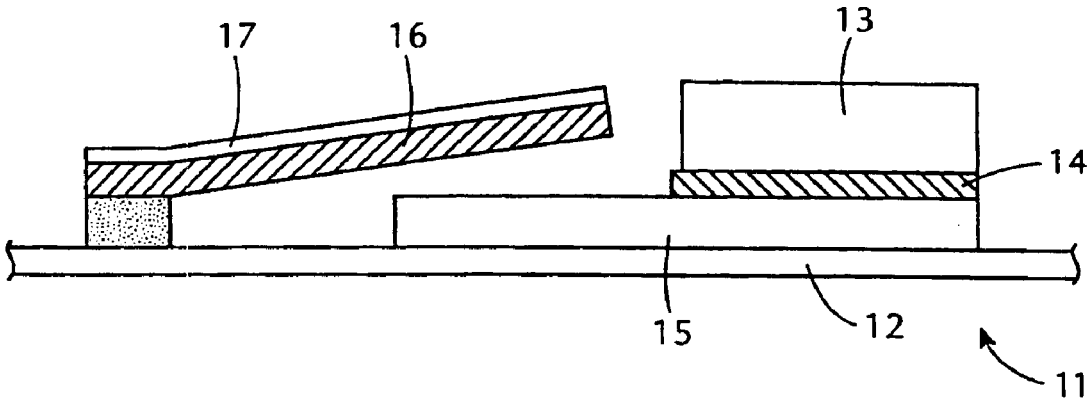

With regard to the well-known temperature dependency of enzymatic reactions, the geometric arrangement of the test design can also be so chosen that the cholesterol test is separated by time from the previous reaction steps. This also allows a controlled regulation of the temperature of the test step. A corresponding test construction is outlined in DE-A-3130749. The preferred construction of a rapid diagnostic agent for HDL in a test strip form (11) is shown in FIG. 2. A fibre mesh (15), a carrier through which liquids can flow and which contains a precipitating agent (14) as well as a separating layer for cellular components (13) are mounted on top of one another on a supporting foil (12). The fibre mesh (15) protrudes from under the carriers (13) and (14) towards a flap. The flap, which consists of a transparent foil (17) and a test film for cholesterol (16) is attached to the supporting foil (12) via an adhesive join (18).

The sample to be investigated is applied to the layer (13) and flows through the layers (14) and (15), during which the non-HDL lipoproteins are separated, into the mesh (15) under the flap. The test reaction is started by pressing the flap with the test layer (16) onto the layer (15). The change in colour can be followed by means of a photometer or a reflection photometer.

In this case in comparison with the embodiment outlined in FIG. 1 lateral separating capacity of the fibre mesh is also effective.

The method according to the present invention has other major advantages over the known methods. It is possible to also use particularly small liquid volumes. The handling of the device according to the present invention is very simple. Only two basic handling steps are necessary, namely the application of a liquid sample and the reading of a measurement after a particular time. Other instruments are not needed apart from a suitable photometer in the case of a quantitative determination. Transfer steps are not needed. All types of blood, even whole blood, can be easily used when a separating pad for cells is used first. If anticoagulants have been added to the sample to be examined, it is recommended that their effects on the determination be compensated. The separation of non-HDL lipoproteins can be carried out in less than 60 sec. The dosage of the sample volume is greatly simplified.

Examples for the invention are given in the following:

EXAMPLE 1

Precipitating agent carrier (14 or 4) for EDTA plasma

A multifilament polyester fabric (100 μm mesh size, 105 μm fabric thickness, 55 threads per cm, with 815 l water passage per $m^2$ and sec) is impregnated with a solution of the following composition:

| | |
|---|---|
| Hepes buffer, 50 mM: pH 7.0 | 78.00 g |
| magnesium acetate × $4H_2O$ | 15.68 g |
| dextran sulphate (MW 50000) | 2.57 g |
| bovine serum albumin | 1.78 g |

A coating of ca 57 ml/$m^2$ is obtained.

After drying under a flow of warm air the impregnated fabric is cut into suitable unit areas which match the corresponding test procedure and they are integrated into the test construction.

EXAMPLE 2

Precipitating agent carrier (14 or 4) for serum

The following impregnating solution is used in the procedure analogous to Example 1:

| | |
|---|---|
| Hepes buffer, 50 mM: pH 7.0 | 78.00 g |
| magnesium acetate × $4H_2O$ | 10.10 g |
| dextran sulphate (MW 50000) | 2.57 g |
| bovine serum albumin | 1.78 g |
| $H_2O$ | 5.58 g |

EXAMPLE 3

Precipitating agent carrier (14 or 4) for blood

A paper of suitable thickness and absorptivity e.g. tea bag paper with a weight per unit area of 12 g/$cm^2$ and a thickness of 50 μm is impregnated with the following impregnating solution:

| | |
|---|---|
| Hepes buffer, 50 mM: pH 7.0 | 70.20 g |
| magnesium acetate × $4H_2O$ | 4.78 g |
| dextran sulphate (MW 50000) | 2.54 g |
| bovine serum albumin | 1.60 g |
| $H_2O$ | 7.80 g |

A coating of ca. 63 ml/$m^2$ is obtained with this carrier.

EXAMPLE 4

Test film

A dispersion of the following composition:

| | |
|---|---|
| K/Na phosphate buffer, 0.5 M; pH 7.0 | 17.14 g |
| Keltrol F | 0.19 g |
| TiO.sub.2 (powder) | 0.31 g |
| dioctyl sodium sulphosuccinate | 0.40 g |
| polyvinylpropionate dispersion (50% in H.sub.2 O) | 11.70 g |
| diatomaceous earth (Celatom MW 25) | 17.65 g |
| phenylsemicarbazide | 0.025 g |
| 2(4-hydroxy-3,5-dimethoxyphenyl)-4-(4-dimethyl-aminophenyl)-5-methyl-imidazole-dihydrochloride | 0.061 g |
| methanol | 1.74 g |
| H.sub.2 O | 46.28 g |
| cholesterol esterase | 23700 U |
| cholesterol oxidase | 6500 U |
| peroxidase | 230000 U |
| hexanol | 2.07 g |

is prepared for the production of a reagent film in order to quantity HDL cholesterol.

The dispersion is applied as a layer of 300 μm thickness onto a polycarbonate foil and dried with warm air. The reagent coating which results forms a graded blue colouration with fluids containing cholesterol depending on the cholesterol content.

| cholesterol concentration | remission R % (measurements in the reflection photometer Reflotron ®) |
|---|---|
| 0 | 70.0 |
| 20 | 43.0 |
| 40 | 29.0 |
| 60 | 22.0 |
| 80 | 18.5 |
| 100 | 16.0 |

EXAMPLE 5

Fibre mesh

Mixture of borosilicate glass fibres with a fibre diameter of ca. 0.6 μm and cellulose fibres with a fibre diameter of ca. 4 μm, preferably in the ratio of 9:1. Weight per unit area ca. 25 g/$m^2$ at a mesh thickness of ca. 0.21 mm; ability of the mesh to take up water of ca. 370 g/$m^2$.

EXAMPLE 6

Production of a rapid diagnostic agent (11) for the determination of HDL

If the test construction of FIG. 2 is chosen, the following measurements apply for the different layers:

| | |
|---|---|
| 12 | 100 × 6 mm |
| 13 | 5 × 6 mm (borosilicate fleece according to DE-A-3029579, weight per unit area ca. 60 g/m$^2$) |
| 14 | 6 × 6 mm |
| 15 | 16 × 6 mm |
| 16/17 | 15 × 6 mm |

This embodiment is suitable for a sample volume between 28–32 μl and is particularly advantageous.

It will be understood that the specification and examples are illustrative but not limitative of the present invention and that other embodiments within the spirit and scope of the invention will suggest themselves to those skilled in the art.

We claim:

1. Apparatus for separating non high density lipoprotein (non-HDL) from a lipoprotein containing body fluid sample, said apparatus comprising:

(i) a first porous carrier which permits flow-through of said lipoprotein containing body fluid sample and which contains a releasable precipitating agent for said non-HDL, said releasable precipitating agent being soluble in said lipoprotein containing body fluid sample; and (ii) a second porous carrier which permits flow-through of said lipoprotein containing body fluid sample but which retains precipitated non-HDLs.

2. Apparatus for determining high density lipoprotein (HDL) cholesterol in a HDL and non high density lipoprotein (non-HDL) containing body fluid sample, said apparatus comprising:

(i) a first porous carrier which permits flow-through of said lipoprotein containing body fluid sample and which contains a releasable precipitating agent for said non-HDL, said releasable precipitating agent being soluble in said lipoprotein containing body fluid sample;

(ii) a second porous carrier which permits flow-through of said lipoprotein containing body fluid sample but which retains precipitated non-HDL; and (iii) an agent for determining cholesterol as a measure for HDL cholesterol.

3. The apparatus of claim 1 wherein at least one of said first and second porous carrier layers is fibrous.

4. The apparatus of claim 3 wherein both of said first and second porous [carriers] *carrier* layers [if] *is* fibrous.

5. The apparatus of claim 2 wherein at least one of said first and second porous carrier layers is fibrous.

6. The apparatus of claim 5 wherein both of said first and second porous carrier layers are fibrous.

* * * * *